United States Patent [19]

Fujino et al.

[11] Patent Number: 4,680,822
[45] Date of Patent: Jul. 21, 1987

[54] BEDDING INCORPORATING FAR INFRARED RADIATOR

[75] Inventors: Yukio Fujino, Tokyo; Morihiro Kabaya, Yokosuka, both of Japan

[73] Assignee: Nishikawa Sangyo Co., Ltd., Tokyo, Japan

[21] Appl. No.: 838,978

[22] Filed: Mar. 12, 1986

[30] Foreign Application Priority Data

Mar. 20, 1985 [JP] Japan .................................. 60-57294

[51] Int. Cl.$^4$ ......................... A47C 21/04; A47G 9/00
[52] U.S. Cl. ........................................... 5/421; 5/448; 5/482; 128/399
[58] Field of Search ................... 5/448, 482, 421, 434, 5/436, 502, 500; 128/399, 402, 403, 376, 377

[56] References Cited

U.S. PATENT DOCUMENTS 4,139,920  2/1979  Evans ...................................... 5/455
4,574,411  3/1986  Yaki ....................................... 5/434

OTHER PUBLICATIONS

Utilization of Far Infrared Rays and Their Effect on Living Bodies.
Growth of Rats Exposed to Far-Infrared Radiation by S. Inoue & K. Honda.
Sleep-Enhancing Effects of Far-Infrared Radiation in Rats by K. Honda & S. Inoue.
Encyclopaedia Chimica.

Primary Examiner—Alexander Grosz
Attorney, Agent, or Firm—Armstrong, Nikaido, Marmelstein & Kubovcik

[57] ABSTRACT

A bedding incorporates a piece or pieces of an alumina, zirconium, silicon or other specified far infrared radiating ceramic which radiates electromagnetic waves with a peak wavelength of 8 to 14 μm when heated, particularly, to a temperature approximately equal to the human body temperature.

2 Claims, 6 Drawing Figures

BEDDING INCORPORATING FAR INFRARED RADIATOR

FIELD OF THE INVENTION AND RELATED ART STATEMTNT

The present invention relates to a bedding including a far infrared radiator which radiates electromagnetic waves with a peak wavelength of 8 to 14 μm at a temperature approximately equal to the human body temperature.

Most of the infrared rays hitherto used for irradiation have been the so-called near infrared rays with the wavelength of from 0.76 μm to 4.0 μm (exclusive). The infrared rays with such wavelength are out of the infrared-rays absorption range of the human body, i.e., 4 to 50 μm, particularly 8 to 14 μm. Therefore, such infrared rays do not penetrate into the human body to warm it up from inside and can warm up only the surface of the human body so that a user may not feel very comfortable upon being exposed to the infrared rays. In addition, the effect of such infrared rays appears only at the surface of the skin and in some cases, the user's skin gets scorched even at a low temperature.

It is well known that ceramics radiate far infrared rays when heated up to a high temperature. Such ceramics, an example of which is a zirconia ceramic as disclosed in Japanese Patent Publication No. 49-31723 (1974), are widely used as refractories and heat-resistant porcelain. An infrared heater in which such a ceramic is heated up to a high temperature is produced by forming the ceramic material into a plate or a tube and providing an electric, gas or other heating means for heating the ceramic member to a high temperature thereby causing the member to radiate infrared rays, as disclosed, for instance, in Japanese Patent Publication No. 47-25010 (1972).

Hitherto, in utilization of the infrared radiators for warming the human body, there has been only a method of heating a ceramic up to a high temperature and irradiating the human body with the far infrared rays radiated from the ceramic. Therefore, the range of application of such a method has been extremely limited, and such a far infrared radiator could not be utilized by incorporating in the same in bedding.

OBJECT AND SUMMARY OF THE INVENTION

It is an object of the present invention to provide a bedding which is comfortable, has a good effect for sound sleeping and has remarkable effects on the health of persons.

According to the present invention, the bedding includes a piece or pieces of an alumina, zirconium, silicon or other specified far infrared radiating ceramic which radiates electromagnetic waves with a peak wavelength of from 8 to 14 μm when heated, particularly, to the temperature approximately equal to the human body temperature, namely, 35.5° to 36.5° C.

The far infrared radiating ceramic constituting the far infrared radiator used here is obtained by mixing an ordinary clay the *kibushi* clay, a kind of kaolinite clay, adding pulverized silica stone to the resultant mixture used as a base material, further adding aluminum oxide, zirconium oxide or silicon oxide to the admixture, kneading the thus obtained mixture together with water, molding the thus kneaded mixture into scales or tablets, and firing the scales or tablets at a high temperature of 1250° to 1450° C. according to the usual method.

The alumina, zirconium or silicon ceramic thus obtained can easily radiate the infrared rays with a peak wavelength of 8 to 14 μm conforming to the infrared ray absorption range of the human body when warmed to a temperature of about 35.5° to 36.5° C. Accordingly, a bedding including such a ceramic has been successfully obtained.

The bedding according to the present invention includes the far infrared radiator or radiators capable of radiating electromagnetic waves with a peak wavelength of 8 to 14 μm when warmed to a temperature of 35.5° to 36.5° C. which is approximately equal to the human body temperature; therefore, when a person sleeps on the bedding, far infrared rays conforming to the infrared ray absorption range of the human body are radiated from the radiator or radiators included in the bedding warmed by the user's body heat, and penetrate into the user's body to a depth of from 40 to 50 mm beneath the skin, resulting in the radiant energy being absorbed in the user's body activating the cells and warming up the body from the inside.

DETAILED DESCRIPTION OF PREFERRED EMBODIMENTS

The bedding including a far infrared radiator according to the present invention will now be explained referring to the attached drawings.

Figure 1:
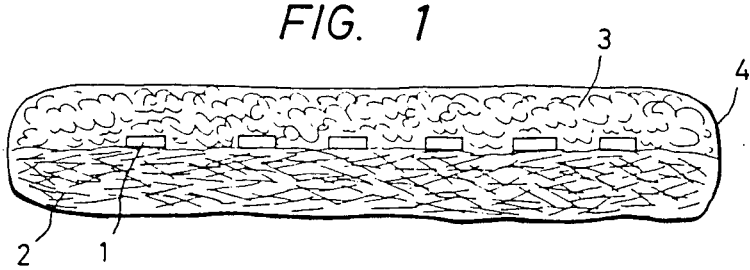
FIG. 1 is a cross-sectional view of an embodiment of a mattress of the bedding according to the present invention.
Figure 2:
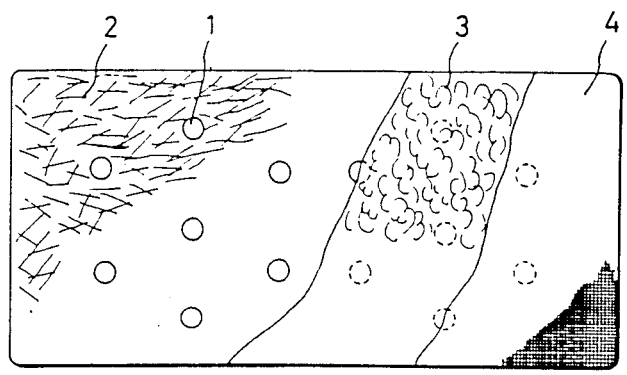
FIG. 2 is a partially cutaway plan view of the embodiment of FIG. 1.

FIG. 1 and 2 illustrate an example of a mattress including the far infrared radiators, in which numeral 1 is the far infrared radiators placed on a felt 2 formed from cotton, chemical fibers, and synthetic fibers or a mixture thereof, and numeral 3 is the fillings covering the upper surfaces of the radiators, the whole body being enveloped in ticking 4. In order to obtain a good warming effect by the body heat and a good radiating effect of far infrared rays, it is preferable to locate the far infrared radiators close to the surface of the mattress, unless it is uncomfortable for the user. In addition, it is suitable to arrange the radiators in a few rows along the longitudinal direction at a central part of the mattress, as shown in FIG. 2.

Figure 3:
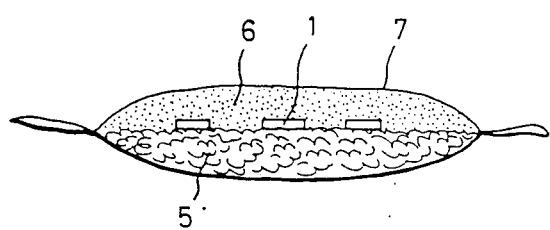
FIG. 3 is a cross-sectional view of an embodiment of a pillow of the bedding according to the present invention.
Figure 4:
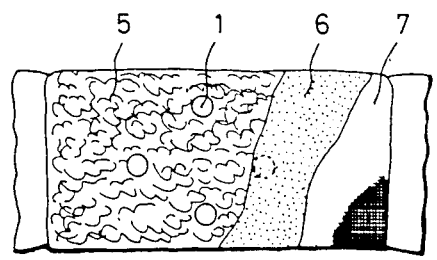
FIG. 4 is a partially cutaway plan view of the embodiment of FIG. 3.

Next, FIGS. 3 and 4 illustrate a pillow comprising the far infrared radiators 1 disposed between kapok 5 and buckwheat chaff 6, the whole body being enveloped in a sack 7.

Figure 5:
FIGS. 5 and 6 are each a perspective view of a far infrared radiator used in the present invention.
Figure 6:

The far infrared radiating ceramic constituting the far infrared radiator used in the present invention can be obtained in the form of scales or tablets as shown in FIG. 5 or 6, respectively, by mixing an ordinary clay with *kibushi* clay, a kind of kaolinite clay in Japan, adding pulverized silica stone to the resultant mixture used as a base material, further adding aluminum oxide, zirconium oxide or silicon oxide to the admixture, kneading the thus obtained mixture together with water, molding the thus kneaded mixture into scales or tablets, and firing the scales or tablets at a high temperature of 1250° to 1450° C. according to the usual method. In the explanation of the working example of the present invention above, the mattress has been explained as one comprising the far infrared radiators disposed between the felt and the fillings, the whole body being enveloped in the ticking. However, it goes without saying that a mattress according to the present invention is not limited to the mattress of the above-mentioned construction but may be formed of any other blank materials, provided that the far infrared radiators are located at intermediate parts thereof.

Also, the construction of a pillow according to the present invention is not limited to the combination of kapok and buckwheat chaff explained in the above example, and the pillow may be formed from the kapok only, or the buckwheat chaff only, or may be a sponge pillow, a sand pillow or the like, provided that the far infrared radiators are included therein.

Further, the bedding according to the present invention is not limited to a mattress or pillow, but includes various other articles of bedding such as a coverlet and a blanket, including the far infrared radiator or radiators therein.

As described above, the bedding according to the present invention includes the far infrared radiator or radiators capable of radiating electromagnetic waves with a peak wavelength of 8 to 14 $\mu$m conforming to the infrared absorption band of the human body when heated to a temperature of 35.5° to 36.5° C. which is approximately equal to the human body temperature; therefore, when a person is asleep in the bedding, far infrared rays are radiated from the far infrared radiators included in the bedding warmed up by his body heat, the radiant energy absorbed into his body activates the cells and warms the body from the inside, resulting in dilatation of capillary vessels, stimulation of the circulation of the blood, strengthening of metabolism. Accordingly, the present invention provides a bedding which is comfortable, has a good effect for sound sleeping and has remarkable effects on the health of sick persons, bed-ridden aged persons, or the like.

We claim:

1. A bedding item comprising a far infrared wave radiating material therein, which material, when warmed up to approximately 36° C. by human body heat, radiates electromagnetic waves with a peak wavelength of from 8 to 14 $\mu$m.

2. A bedding according to claim 1, wherein the far infrared radiator is formed of a ceramic selected from the group consisting of alumina ceramics, zirconium ceramics and silicon ceramics.

* * * * *